(12) United States Patent
Ehlert et al.

(10) Patent No.: US 9,980,705 B2
(45) Date of Patent: May 29, 2018

(54) TISSUE BIOPSY DEVICE WITH SELECTIVELY ROTATABLY LINKED THUMBWHEEL AND TISSUE SAMPLE HOLDER

(71) Applicant: DEVICOR MEDICAL PRODUCTS, INC., Cincinnati, OH (US)

(72) Inventors: John Scott Ehlert, Cincinnati, OH (US); Edward A. Rhad, Fairfield, OH (US); Jessica Pyzoha Leimbach, Cincinnati, OH (US); Morgan Robert Hunter, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days. days.

(21) Appl. No.: 15/267,753

(22) Filed: Sep. 16, 2016

(65) Prior Publication Data

US 2017/0000465 A1    Jan. 5, 2017

Related U.S. Application Data

(63) Continuation of application No. 13/800,502, filed on Mar. 13, 2013, now Pat. No. 9,474,511.

(60) Provisional application No. 61/711,026, filed on Oct. 8, 2012.

(51) Int. Cl.
*A61B 5/00* (2006.01)
*A61B 10/02* (2006.01)
*A61B 10/00* (2006.01)

(52) U.S. Cl.
CPC ...... *A61B 10/0233* (2013.01); *A61B 10/0096* (2013.01); *A61B 10/0283* (2013.01); *A61B 2010/0208* (2013.01)

(58) Field of Classification Search
CPC . A61B 10/02; A61B 10/0233; A61B 10/0283; A61B 2010/0208; A61B 2010/0225
See application file for complete search history.

(56) References Cited

U.S. PATENT DOCUMENTS

| 5,526,822 A | 6/1996 | Burbank et al. |
| 5,649,547 A | 7/1997 | Ritchart et al. |
| 5,769,086 A | 6/1998 | Ritchart et al. |

(Continued)

FOREIGN PATENT DOCUMENTS

| CN | 102217954 A | 10/2011 |
| CN | 102499720 A | 6/2012 |

OTHER PUBLICATIONS

Chinese Office Action dated Jul. 6, 2016 for Application No. 201380064151.7, 10 pages.

(Continued)

*Primary Examiner* — Max Hindenburg
(74) *Attorney, Agent, or Firm* — Frost Brown Todd LLC

(57) ABSTRACT

A biopsy system comprising a probe and a holster. The probe comprises a rotatable needle portion a rotatable thumbwheel coupled with the needle portion and a rotatable tissue sample manifold. The holster is removably coupled to the probe. The holster comprises a selective engagement mechanism configured to selectively link rotation of the thumbwheel with rotation of the tissue sample manifold. A method of collecting tissue samples using a biopsy system unlinking rotation of the thumbwheel with rotation of the tissue sample manifold by actuating the selective engagement mechanism; and obtaining a tissue sample after the unlinking.

20 Claims, 12 Drawing Sheets

(56) References Cited

U.S. PATENT DOCUMENTS

| | | |
|---|---|---|
| 5,775,333 A | 7/1998 | Burbank et al. |
| 5,928,164 A | 7/1999 | Burbank et al. |
| 5,964,716 A | 10/1999 | Gregoire et al. |
| 5,980,469 A | 11/1999 | Burbank et al. |
| 6,007,497 A | 12/1999 | Huitema |
| 6,017,316 A | 1/2000 | Ritchart et al. |
| 6,077,230 A | 6/2000 | Gregoire et al. |
| 6,086,544 A | 7/2000 | Hibner et al. |
| 6,120,462 A | 9/2000 | Hibner et al. |
| 6,228,055 B1 | 5/2001 | Foerster et al. |
| 6,231,522 B1 | 5/2001 | Voegele et al. |
| 6,273,862 B1 | 8/2001 | Privitera et al. |
| 6,283,925 B1 | 9/2001 | Terwilliger |
| 6,662,971 B1 | 12/2003 | Nguyen et al. |
| 6,689,072 B2 | 2/2004 | Kaplan et al. |
| 7,104,994 B1 | 9/2006 | Amis et al. |
| 7,419,472 B2 | 9/2008 | Hibner et al. |
| 7,740,597 B2 | 6/2010 | Cicenas et al. |
| 7,867,173 B2 | 1/2011 | Hibner et al. |
| 7,922,699 B2 | 4/2011 | Baba et al. |
| 7,938,786 B2 | 5/2011 | Ritchie et al. |
| 8,002,713 B2 | 8/2011 | Heske et al. |
| 8,075,229 B2 | 12/2011 | Mok et al. |
| 8,251,916 B2 | 8/2012 | Speeg et al. |
| 8,480,595 B2 | 7/2013 | Speeg et al. |
| 8,597,206 B2 | 12/2013 | Videback |
| 8,628,482 B2 | 1/2014 | Leimbach et al. |
| 2003/0199753 A1 | 10/2003 | Hibner et al. |

OTHER PUBLICATIONS

Extended European Search Report dated Aug. 11, 2016 for Application No. 138580840, 6 pages.
International Search Report and Written Opinion dated Dec. 30, 2013 for Application No. PCT/US2013/063079.
U.S. Appl. No. 61/682,418, filed Aug. 13, 2012.

TISSUE BIOPSY DEVICE WITH SELECTIVELY ROTATABLY LINKED THUMBWHEEL AND TISSUE SAMPLE HOLDER

This application is a continuation of U.S. Ser. No. 13/800,502, entitled "TISSUE BIOPSY DEVICE WITH SELECTIVELY ROTATABLY LINKED THUMBWHEEL AND TISSUE SAMPLE HOLDER," filed on Mar. 13, 2013, published as U.S. Pub. No. 2014/0100477 on Apr. 10, 2014, which claims priority to U.S. Provisional Application No. 61/711,026, titled "TISSUE BIOPSY DEVICE WITH SELECTIVELY ROTATABLY LINKED THUMBWHEEL AND TISSUE SAMPLE HOLDER," filed on Oct. 8, 2012, the entirety of which is hereby incorporated herein.

BACKGROUND OF THE INVENTION

Field of the Invention

Aspects of the present invention relate in general to biopsy devices, and more particularly to biopsy devices having the capability to store multiple tissue samples, such as in a spaced-apart, sequenced manner, within a portion of the biopsy device.

Background

When a suspicious tissue mass is discovered in a patient's breast or in another area through examination, ultrasound, MRI, X-ray imaging or the like, it may be necessary to perform a biopsy procedure to remove one or more samples of that tissue in order to determine whether the mass contains cancerous cells. A biopsy may be performed using an open or percutaneous method. Medical devices for obtaining tissue samples for subsequent sampling and/or testing are known in the biopsy art. For instance, biopsy instruments now marketed under the tradename MAMMOTOME®, including MAMMOTOME® REVOLVE™ are commercially available from Devicor Medical Products for use in obtaining breast biopsy samples.

An open biopsy may be performed by making a large incision in the breast and removing either the entire mass, called an excisional biopsy, or a substantial portion of it, known as an incisional biopsy. An open biopsy is a surgical procedure that may be done as an outpatient procedure in a hospital or a surgical center, and may involve a high cost and a high level of trauma to the patient. Open biopsy may carry relatively higher risk of infection and bleeding than does percutaneous biopsy, and the disfigurement that may result from an open biopsy may make it difficult to read future mammograms. Further, the aesthetic considerations of the patient might make open biopsy even less appealing due to the potential risk of disfigurement. Given that some biopsies show that the suspicious tissue mass is not cancerous, the potential downsides of the open biopsy procedure might render this method inappropriate in some cases.

Percutaneous biopsy may be less invasive than open biopsy. Percutaneous biopsy may be performed using fine needle aspiration (FNA), core needle biopsy, or otherwise. In FNA, a very thin needle may be used to withdraw fluid and cells from the suspicious tissue mass. This method may be low-pain, so low-pain that local anesthetic is not necessarily always used because the application of it may be more painful than the FNA itself. However, in some FNA procedures, only a small number of cells might be obtained through the procedure, rendering it relatively less useful in some situations in analyzing the suspicious tissue and making an assessment of the progression of the cancer less simple if the sample is found to be malignant.

During some core needle biopsy procedures, a small tissue sample may be removed allowing for a pathological assessment of the tissue, including an assessment of the progression of any cancerous cells that are found.

The biopsy instruments marketed under the trade name MAMMOTOME®, including MAMMOTOME® RESOLVE™ are commercially available from Devicor Medical Products generally retrieve multiple core biopsy samples from one insertion into breast tissue with vacuum assistance. In particular, a cutter tube is extended into a probe to cut tissue prolapsed into a side aperture under vacuum assistance, and then the cutter tube is fully retracted between cuts to extract the sample.

With a device having a relatively long cutter travel, the rate of sample taking may be limited not only by the time required to rotate or reposition the probe but also by the time needed to translate the cutter. As an alternative to relatively "long stroke" biopsy devices, a "short stroke" biopsy device is described in the following: U.S. Pat. No. 7,419,472 issued Sep. 2, 2008; and U.S. Pat. No. 7,740,597 issued Jun. 22, 2010, both of which are incorporated herein by reference. The cutter can be cycled through a distance substantially equal to or slightly greater than the distance across the side aperture, reducing the sample time.

The following patent documents disclose various biopsy devices, and are incorporated herein by reference in their entirety: U.S. Pat. No. 8,083,687 issued Dec. 27, 2011; U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; and US Patent Application Publication No. 2003/0199753 published Oct. 23, 2003 to Hibner et al. U.S. Pat. No. 5,526,822, incorporated by reference above, discloses a tissue sample cassette, including a rotary sample cassette that is belt driven. Other tissue sample storage devices are disclosed in U.S. Pat. No. 7,740,596 issued Jun. 22, 2010; and U.S. Pat. No. 7,867,173 issued Jan. 11, 2011, each of which is incorporated by reference herein. Additionally, U.S. Provisional Application No. 61/682,418, entitled "BIOPSY SYSTEM WITH GRAPHICAL USER INTERFACE," filed on Aug. 13, 2012, which is incorporated by reference herein, discloses a graphical user interface system and method used in conjunction with a biopsy system.

While a variety of biopsy devices have been made and used, and a variety of tissue sample storage devices and techniques have been devised, the above-listed references do not include a biopsy device where rotation of a thumbwheel is selectively linked with rotation of a tissue sample manifold.

SUMMARY OF THE INVENTION

Aspects of the present invention provide, among other things, a biopsy device comprising a probe, the probe having a rotatable needle portion, a rotatable thumbwheel coupled with the needle portion; and a rotatable tissue sample manifold. The biopsy device includes a holster removably coupled to the probe, the holster comprising a selective engagement mechanism configured to selectively link rotation of the thumbwheel with rotation of the tissue sample manifold.

In one example variation the holster includes a motor linked to the tissue sample manifold and selectively linked with the thumbwheel.

In some variations, the selective engagement mechanism has a first configuration where the thumbwheel is linked to the rotation of the tissue sample manifold and a second configuration where the thumbwheel is not linked to the rotation of the tissue sample manifold.

In another variation, a computer controller may be configured to control one or more of the rotation of the tissue sample manifold, actuation of the selective engagement mechanism, and rotation of the thumbwheel.

Additional advantages and novel features of various aspects of the present invention will be set forth in part in the description that follows, and in part will become more apparent to those skilled in the art upon examination of the following or upon learning by practice thereof.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
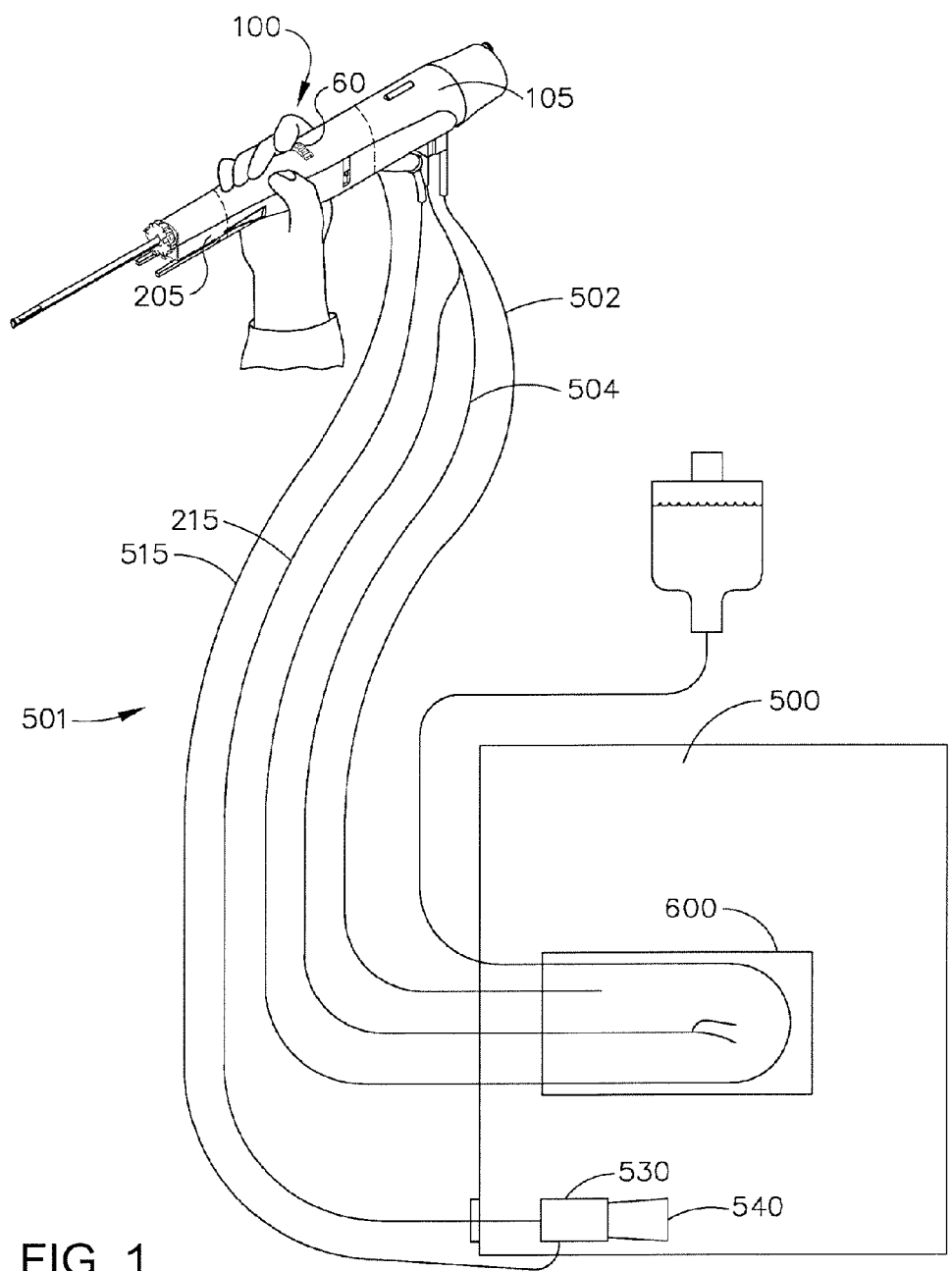
FIG. 1 is a schematic view of a prior art biopsy system and biopsy device.

U.S. Pat. No. 8,083,687 (herein after "the '687 patent") issued on Dec. 27, 2011, which is expressly incorporated by reference herein, illustrates several examples of biopsy devices including a probe with various holsters. FIG. 1 shows a conventional biopsy device 100, having a probe 105 coupled with a holster 205. The biopsy device 100 may be operated in conjunction with a vacuum control module 500 via conduits 501. Vacuum control module 500 is operable to induce a vacuum through vacuum canister 600, and such a vacuum may be communicated to probe 105 via tubes 502, 504. Operation of the vacuum control module is described in detail in the '687 patent and is hereby incorporated by reference herein.

Figure 2:
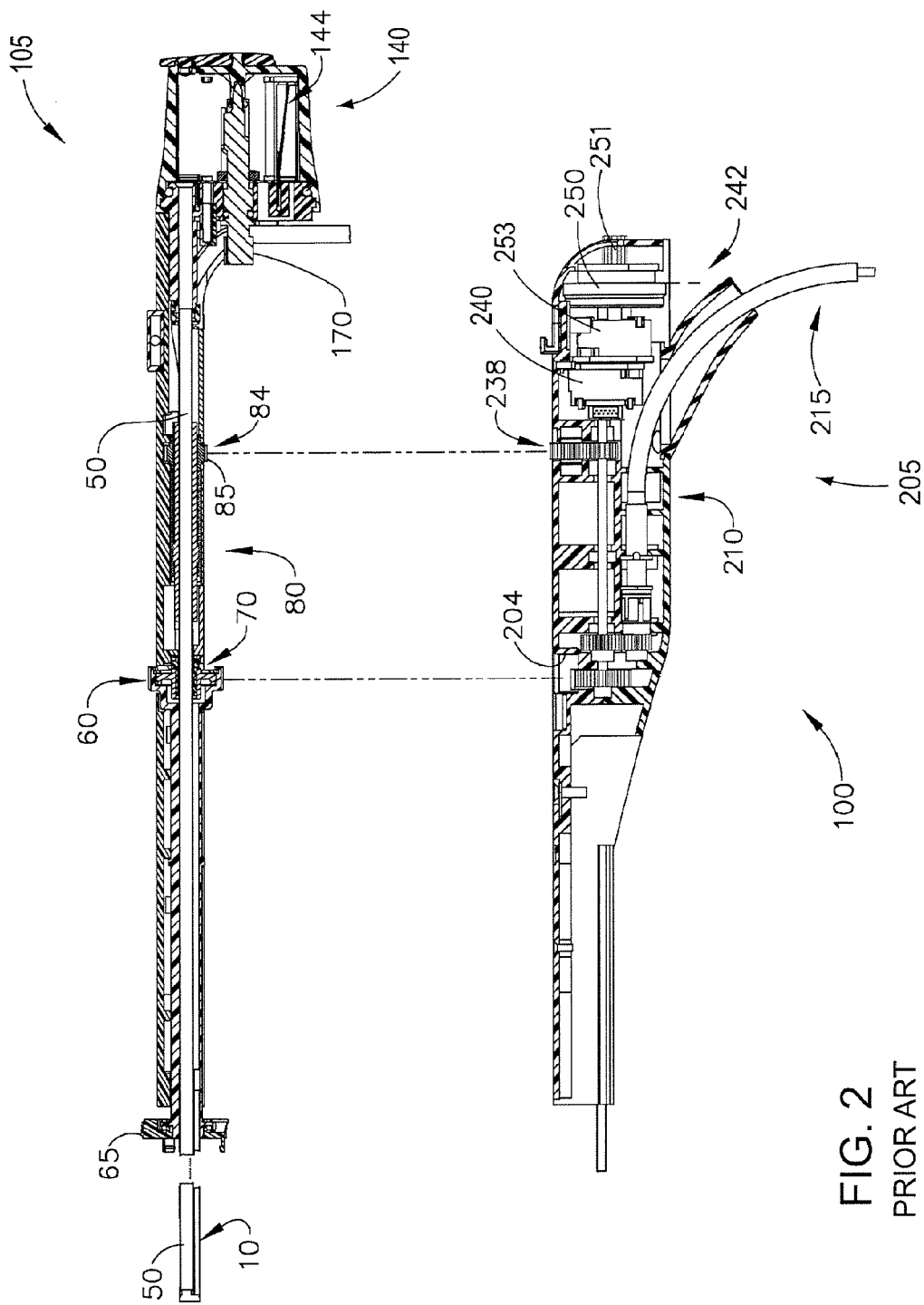
FIG. 2 is a side cross-sectional exploded view of the prior art biopsy device of FIG. 1.

As shown in FIG. 2, the conventional probe 105 broadly generally comprises a needle 10, a cutter 50, a needle orientation indicator 65, thumbwheel 60, a vacuum manifold 70, a cutter rotation and translation mechanism 80, a drive member 84 including a drive gear 85, a sample holder 140 including a rotatable manifold 144, and a holder gear 170. Other aspects of the probe 105 are shown and described in the '687 patent, which is incorporated by reference herein. The conventional holster 205 generally comprises a recess 204, a cutter drive mechanism 210, an intermediate driven gear 238, a tissue sample holder rotation mechanism 242, an encoder assembly 240, 253 and a holder drive gear 251, and a drive cable 215. Other aspects of the conventional holder 205 are shown and described in the '687 patent, which is incorporated by reference herein. The probe 105 couples to the holster 205 such that the thumbwheel 60 is received in the recess 204, the drive gear 85 meshes with the driven gear 238, and the holder gear 170 meshes with the holder drive gear 251. Once engaged, rotational positioning of the manifold 144 is controlled by a piezoelectric motor 250. Software or control logic is used to automatically reposition manifold 144 after each tissue sample is received within an empty chamber and to align a fresh chamber. To acquire a tissue sample, the operator rotates thumbwheel 60 to rotate the needle 10 and the needle orientation indicator 65. The cutter 50 is rotated and translated via the cutter drive mechanism 80, to sever tissue. A vacuum is then applied to tissue sample holder 140 by tube 502, such that the severed tissue sample is drawn down a lumen of the cutter, into a tissue sample passage 54, and finally is deposited into the aligned tissue sample chamber. The details of the process, including operation of the cutter drive mechanism 80, cutter motor 530, motor control 540, and the idler shaft encoder assembly 240, 253, are described in detail in the '687 patent, which is incorporated by reference herein.

Figure 3:
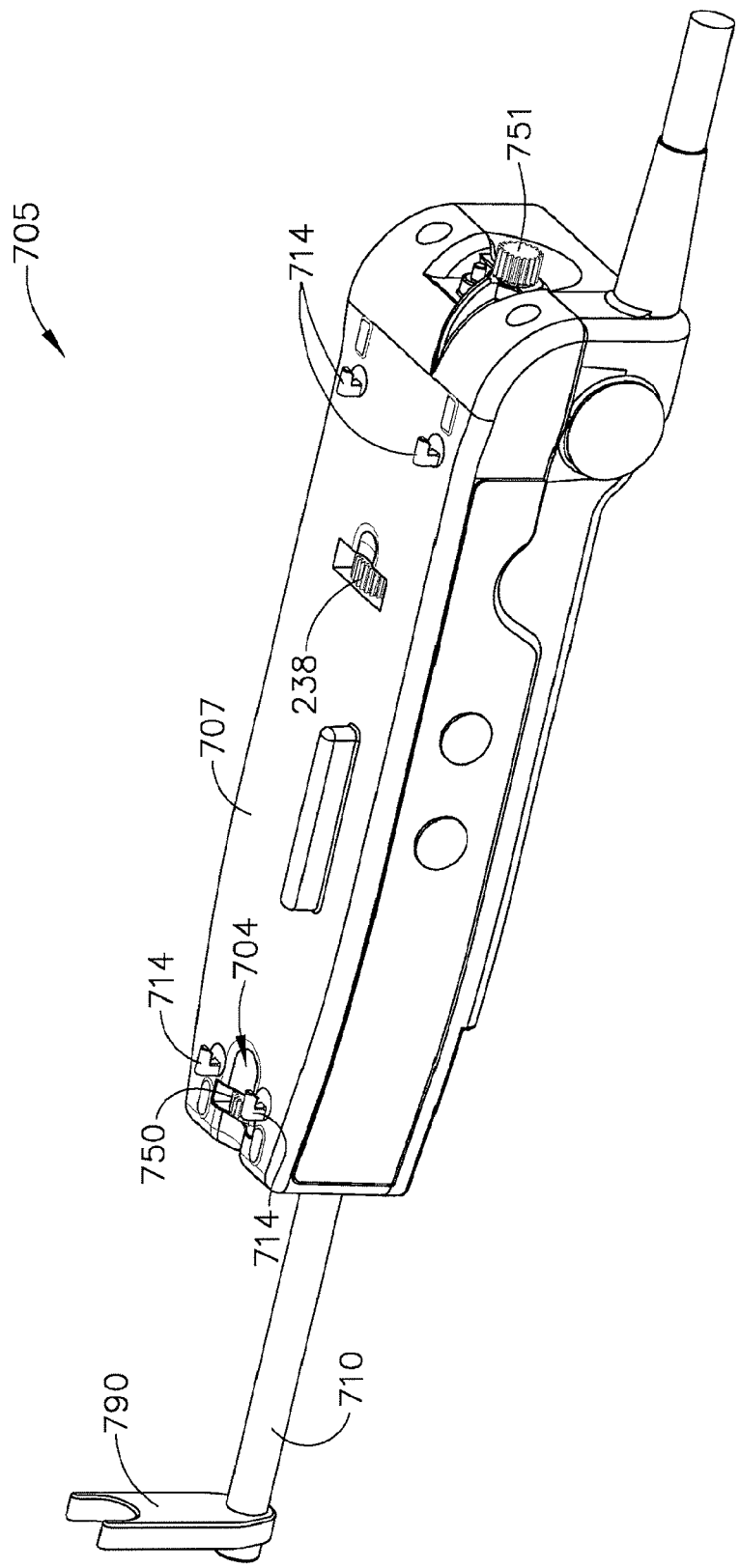
FIG. 3 is a perspective view of a prior art stereotactic holster.
Figure 4:
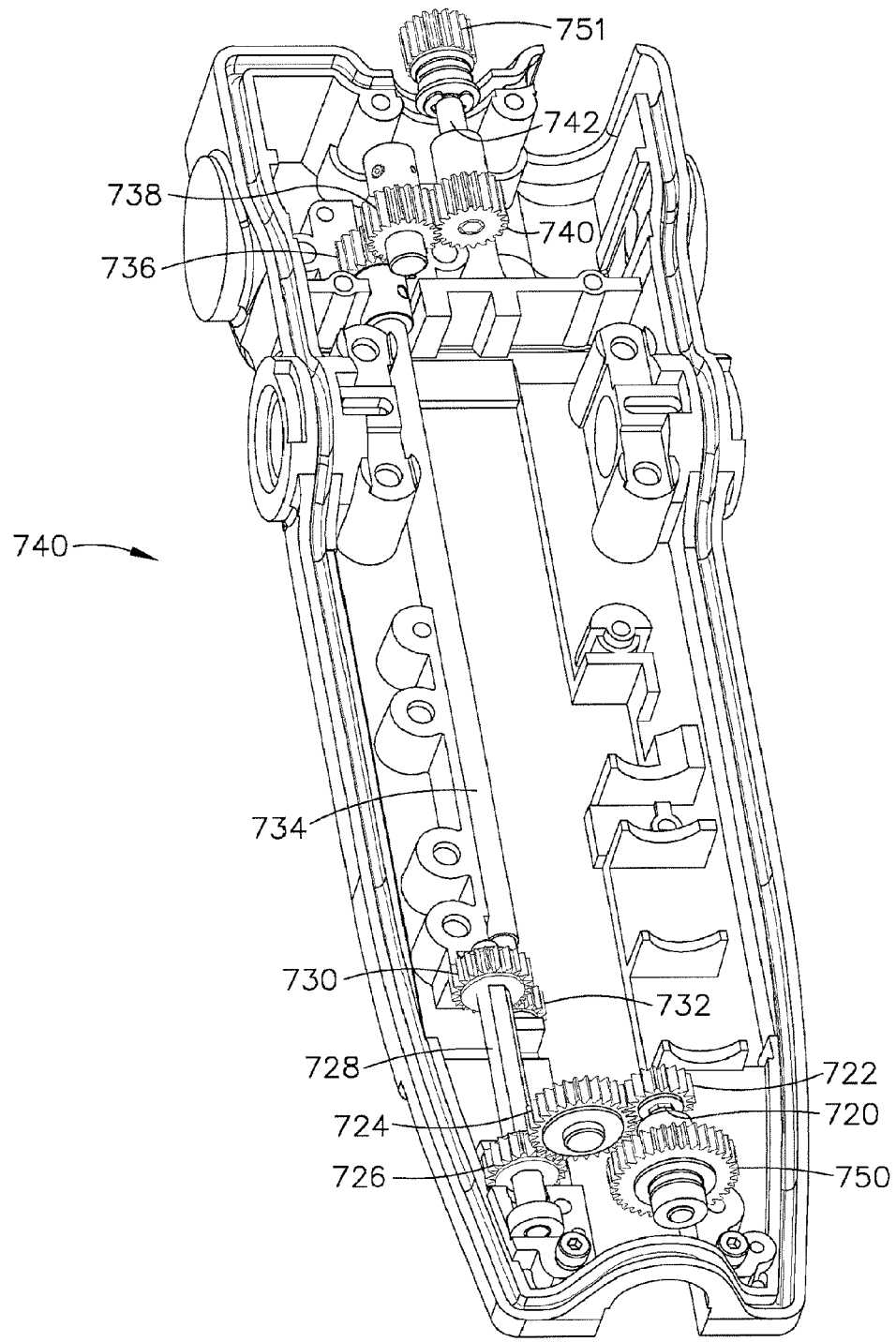
FIG. 4 is a perspective view of the prior art stereotactic holster with components removed.

The '687 patent describes a holster 705, shown in FIGS. 3 and 4, configured for use in a stereotactic setting, which is incorporated by reference herein. The holster 705 may be coupled with probe 105 (FIG. 2), with a probe as described in U.S. Pat. No. 8,251,916 (hereinafter "the '916 patent) issued on Aug. 28, 2012, the disclosure of which is incorporated by reference herein, or with any other suitable probe. Holster 705 comprises a top housing member 707, a bottom housing member 708, and a needle firing fork 790. Needle firing fork 790 is positioned on the distal end of a needle firing shaft 710, which extends distally from holster 705. Holster 705 further comprises hook members 714, which extend from top housing member 707, and which may removably secure probe 105 to holster 705.

Top housing member 707 further comprises a recess 704 exposing a thumbwheel gear 750. Thumbwheel gear 750 is configured to mesh with thumbwheel 60 when probe 105 is coupled with holster 705. In particular, thumbwheel gear 750 is operable to rotate in response to manual rotation of thumbwheel 60 when probe 105 is coupled with holster 705. Thumbwheel gear 750 rotates in the opposite direction as the thumbwheel 60. A tissue sample holder drive gear 751 extends from a proximal end of holster 705. Gear 751 is configured to mesh with gear 170 of tissue sample holder 140. In particular, gear 751 is operable to rotate manifold 144 of tissue sample holder 140 when probe 105 is coupled with holster 705.

As shown in FIG. 4, a linking mechanism 740 links thumbwheel gear 750 with gear 751. In particular, linking mechanism 740 is configured to cause gear 751 to rotate in response to rotation of thumbwheel gear 750. Linking mechanism 740 of this example comprises a shaft 720 extending proximally from thumbwheel gear 750. Another gear 722 is fixed to shaft 720. Gear 722 thus rotates with shaft 720 and with gear 750. Gear 722 also meshes with gear 724, which also meshes with gear 726. Gear 726 thus rotates with gears 722, 724 and in the same direction as gear 722. A shaft 728 extends proximally from gear 726. Another gear 730 is fixed to shaft 728. Gear 730 thus rotates with shaft 728 and with gear 726. Gear 730 also meshes with gear 732. A shaft 734 extends proximally from gear 732. Another gear 736 is fixed to shaft 734 at the distal end of the holster 705. Gear 736 thus rotates with shaft 734 and with gears 730, 732. Gear 736 also meshes with gear 738, which also meshes with gear 740. Gear 740 thus rotates with gears 736, 738 and in the same direction as gear 736. A shaft 742 connects gear 740 with gear 751. Accordingly, thumbwheel gear 750 is coupled with gear 751 via gears 722, 724, 726, 730, 732, 736, 738, 740 and shafts 720, 728, 734, 742.

A cutter drive mechanism not shown is also provided within holster 705. In particular, the cutter drive mechanism is operable to rotate gear 238, which is exposed through top housing member 707. Gear 238 is configured to mesh with gear 85 when probe 105 is coupled with holster 705. Accordingly, rotation of gear 238 causes concomitant rotation and translation of cutter 50 when probe 105 is coupled with holster 705. Exemplary components, features, configurations, and methods of operation for a cutter drive mechanism such as the one in holster 705 are described in the '916 patent, the disclosure of which is incorporated by reference herein.

A needle firing mechanism (not shown) is also provided within holster 705. In particular, the needle firing mechanism is operable to cause shaft 710 and fork 790 to translate longitudinally relative to holster 705. Fork 790 is configured to engage needle portion 10, such that needle portion 10 will translate longitudinally with shaft 710 and fork 790 when probe 105 is coupled with holster 705. Suitable modifications to probe 105 to permit needle portion 10 to translate longitudinally relative to other components of probe 105 will be apparent to those of ordinary skill in the art in view of the teachings herein. Alternatively, any probe disclosed in the '916 patent, the disclosure of which is incorporated by reference herein, may have its needle portion coupled with and translated by fork 790. In either case, such firing of needle portion 10 may be desired to forcibly urge needle portion 10 into breast tissue or other tissue. Exemplary components, features, configurations, and methods of operation for a needle firing mechanism such as the one in holster 705 are described in the '916 patent, the disclosure of which is incorporated by reference herein.

The above structure described by the '687 patent, however, does not allow for disengagement of the coupling of the thumbwheel gear 750 with gear 751. Nor does it allow for linked motor controlled rotation of both the thumbwheel gear 750 and the gear 751.

Figure 5:
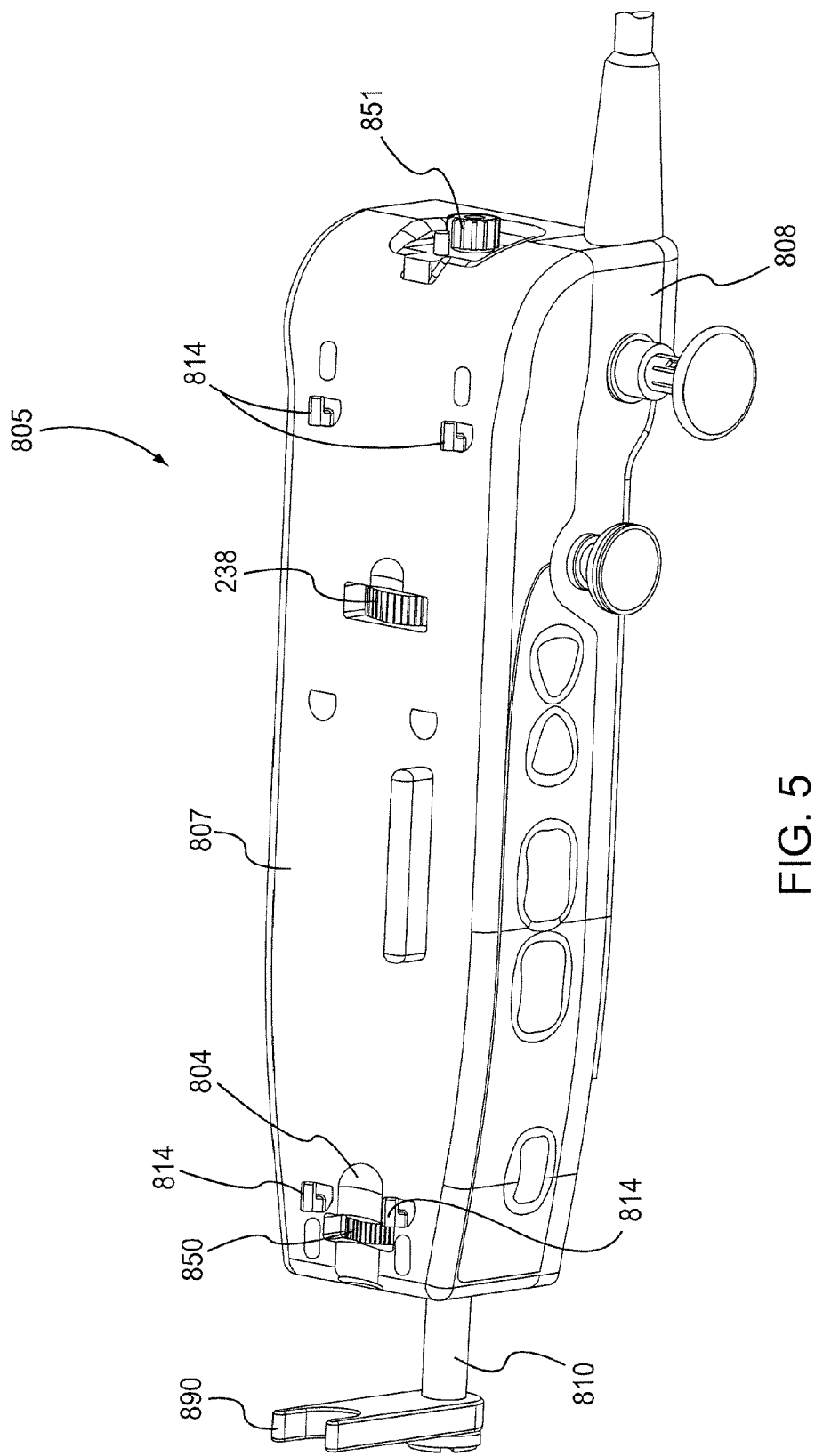
FIG. 5 is a perspective view of a stereotactic holster in accordance with aspects of the present invention.

FIG. 5 shows an example holster 805 in accordance with aspects of the present invention that allows for selective coupling of a thumbwheel of a probe with a holder drive gear. The holster 805 may be coupled with probe 105, with a probe as described in the '916 patent, the disclosure of which is incorporated by reference herein, or with any other suitable probe. Holster 805 comprises a top housing member 807, a bottom housing member 808, and a needle firing fork 890. Needle firing fork 890 is positioned on the distal end of a needle firing shaft 810, which extends distally from holster 805. Holster 805 further comprises hook members 814, which extend from top housing member 807, and which may removably secure a probe to holster 8.

Top housing member 807 further comprises a recess 804 exposing a thumbwheel gear 850. Thumbwheel gear 850 is configured to mesh with thumbwheel 60 when probe 105 is coupled with holster 805. In particular, thumbwheel gear 850 is operable to rotate in response to manual rotation of thumbwheel 60 when probe 105 is coupled with holster 805. A tissue sample holder drive gear 851 extends from a proximal end of holster 805. Gear 851 is configured to mesh with gear 170 of tissue sample holder 140. In particular, gear 851 is operable to rotate manifold 144 of tissue sample holder 140 when probe 105 is coupled with holster 805.

Figure 6:
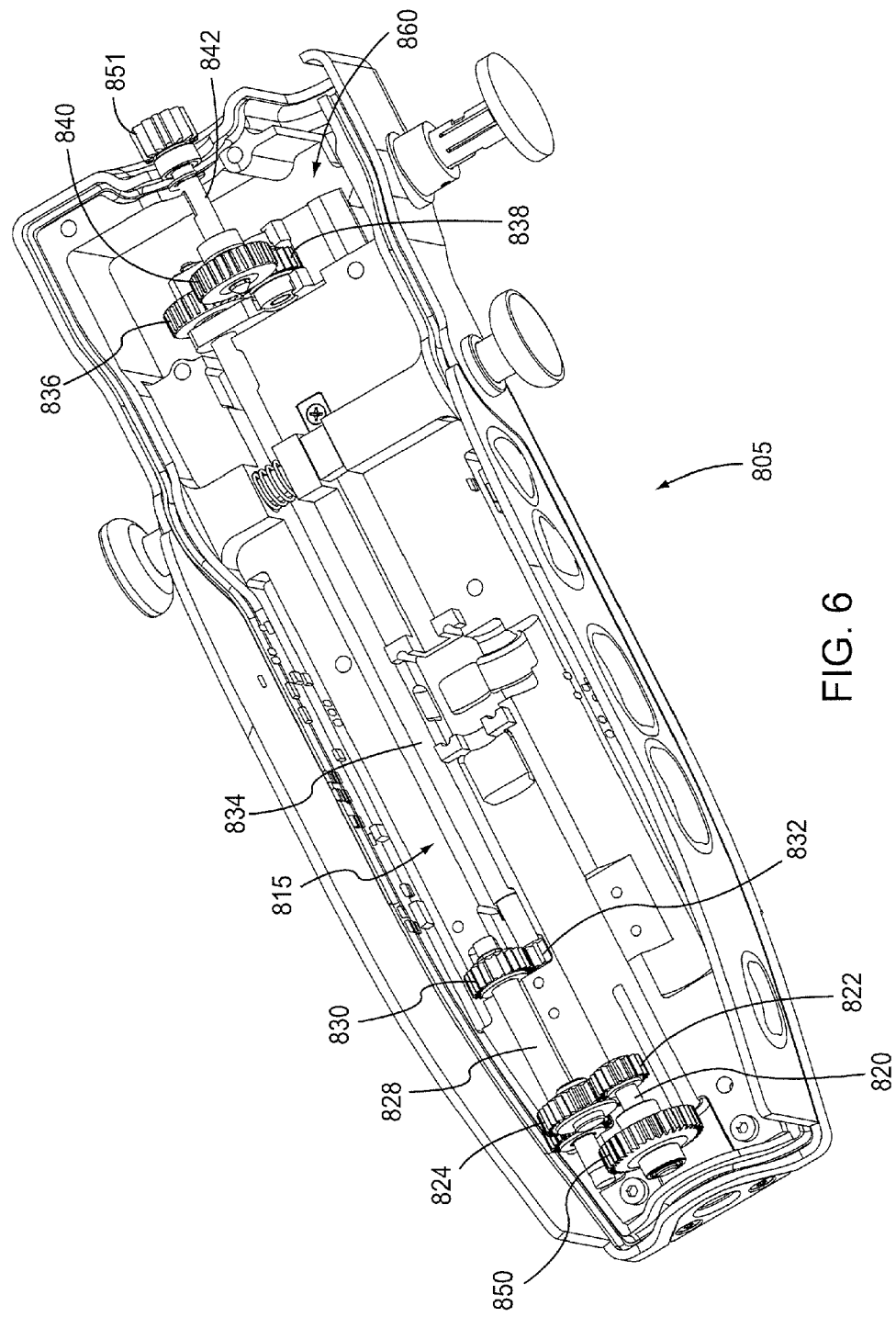
FIG. 6 is a perspective view of the stereotactic holster of FIG. 5, with components removed.
Figure 7:
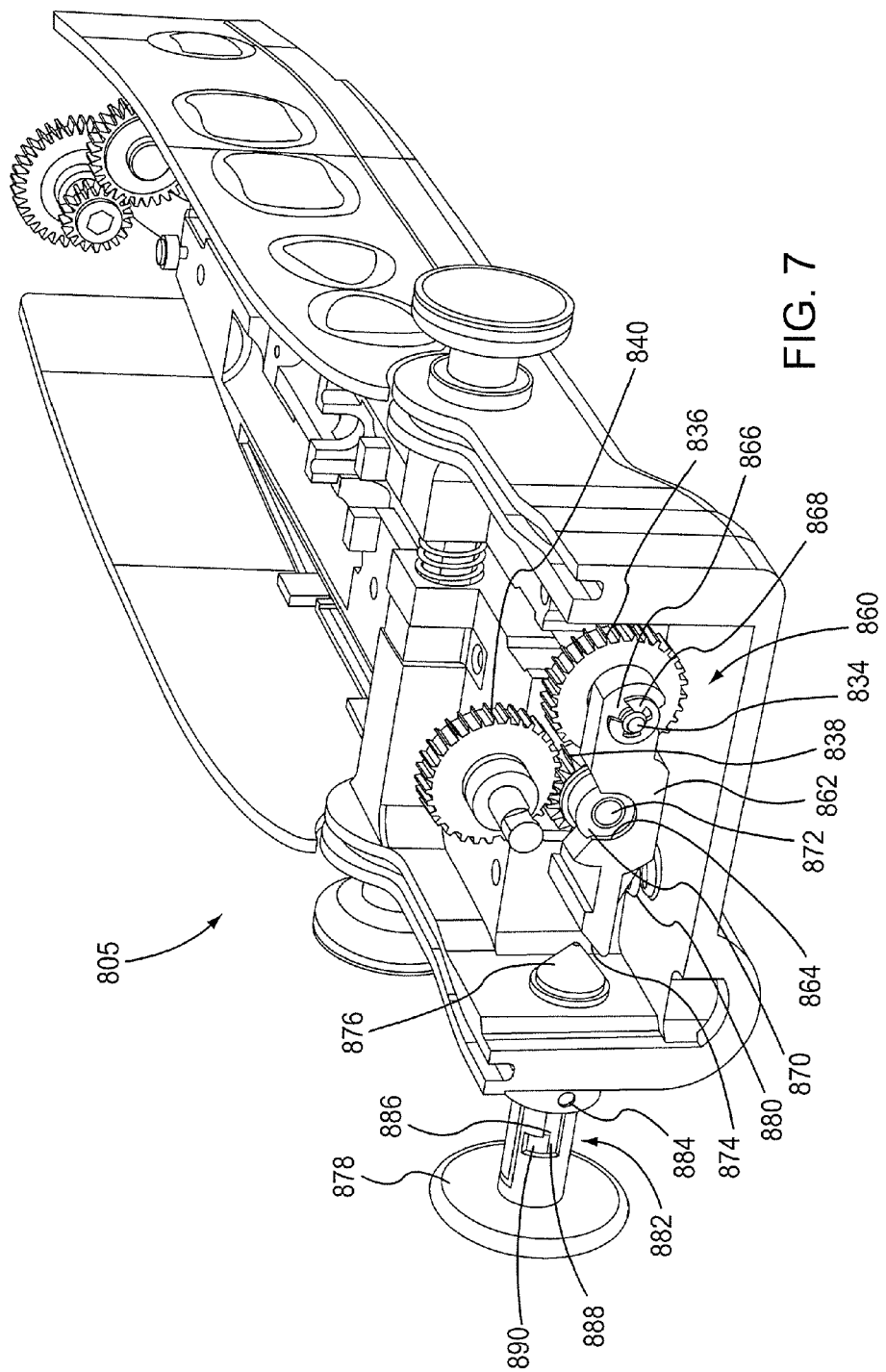
FIG. 7 shows a cut end perspective view of the stereotactic holster of FIG. 5 in an engaged configuration, with components removed.

FIGS. 6 and 7 are perspective views of an example stereotactic 805 with components omitted to show an example linking mechanism and example selective engagement mechanism. A linking mechanism 815 selectively links thumbwheel gear 850 with gear 851. In particular, the linking mechanism 815, having a selective engagement mechanism 860, is configured to selectively cause gear 851 to rotate in response to rotation of thumbwheel gear 850. Linking mechanism 815 of this example comprises a shaft 820 extending proximally from thumbwheel gear 850. Another gear 822 is fixed to shaft 820. Gear 822 thus rotates with shaft 820 and with gear 850. Gear 822 also meshes with gear 824, which also meshes with gear 826. Gear 826 thus rotates with gears 822, 824. A shaft 828 extends proximally from gear 826. Another gear 830 is fixed to shaft 828. Gear 830 thus rotates with shaft 828 and with gear 826. Gear 830 also meshes with gear 832. A shaft 834 extends proximally from gear 832. Another gear 836 is fixed to shaft 834. Gear 836 thus rotates with shaft 834 and with gears 830, 832. Gear 836 meshes with gear 838. Gear 838 selectively meshes with gear 840. When gear 838 is selected to mesh with gear 840, gear 840 thus rotates with gears 836, 838. A shaft 842 connects gear 840 with gear 851. Accordingly, when gear 838 is selected to mesh with gear 840, thumbwheel gear 850 is coupled with gear 851 via gears 822, 824, 826, 830, 832, 836, 838, 840 and shafts 820, 828, 834, 842. However, when gear 838 is selected such that it does not mesh with gear 840, thumbwheel gear 850 is not coupled with gear 851. Accordingly, in the non-meshed configuration, motion of the thumbwheel 60 will not be linked to motion of the tissue sample holder 140 via the holder gear 851.

Figure 8:
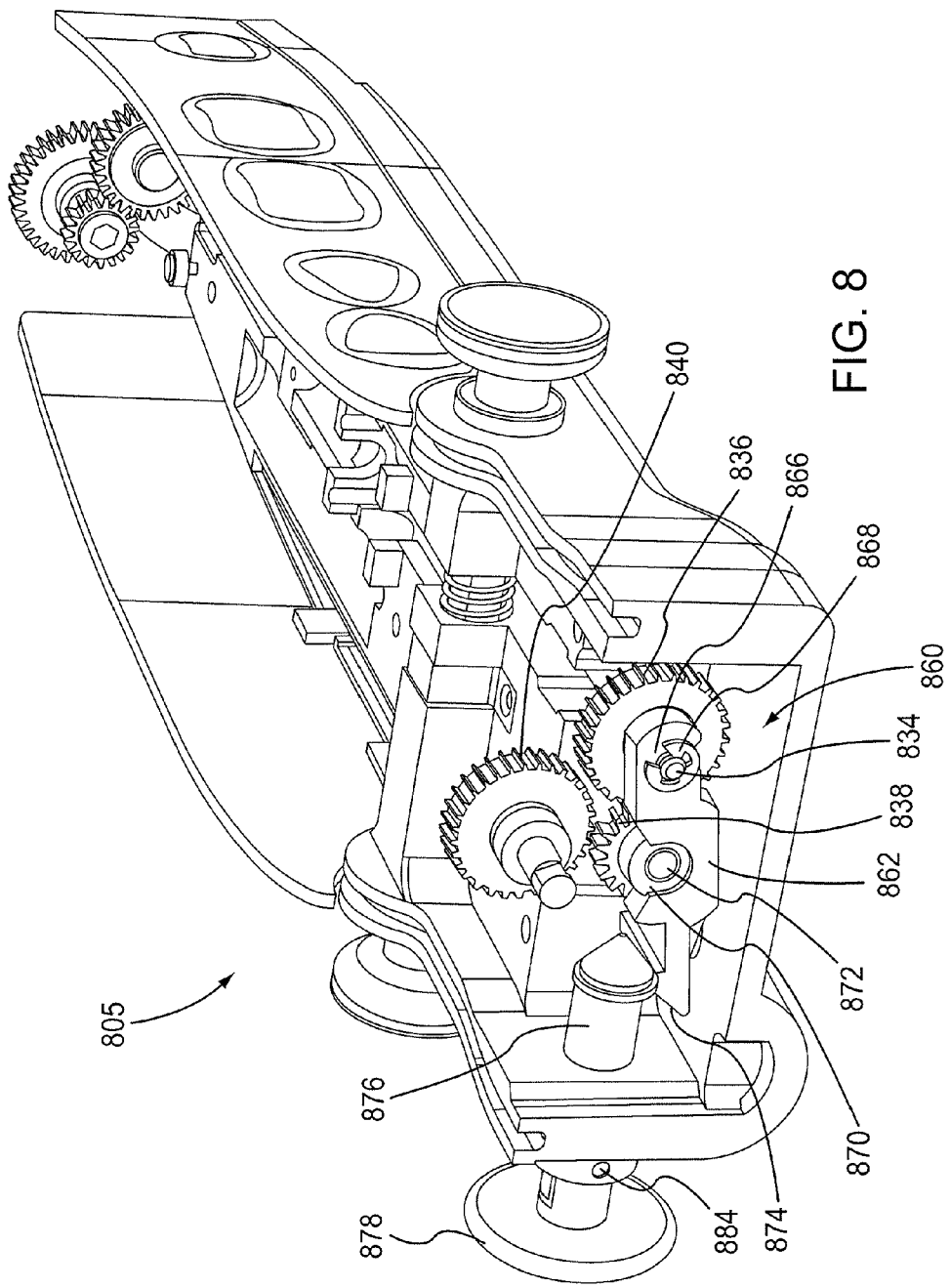
FIG. 8 shows a cut end perspective view of the stereotactic holster of FIG. 5 in a disengaged configuration, with components removed.

The selective meshing of the gear 838 with the gear 840 occurs by actuating the selective engagement mechanism 860. As shown in FIGS. 6-8, the selective engagement mechanism 860 may include a bracket 862 pivotally connected to an end of the shaft 834. The bracket 862 may be attached to the shaft 834 by passing the shaft 834 through receiving holes 866. A clip 868 may be provided to ensure stable attachment of the bracket 862 to the shaft 834. The bracket 862 includes a pair of troughs 864 adjacent to the gear 838 for receiving a pair of retaining features 870. The retaining features 870 and the gear 838 may be attached to the shaft 872. The gear 838 may be located between the pair of retaining features 870. The retaining features 870 rest within the troughs 864 but may freely rotate along with the shaft 872 and the gear 838. Because gear 838 meshes with gear 836, rotation of the gear 836 causes the gear 838 to rotate. The selective engagement mechanism 860 further includes a plunger 878 having a projection 876. The bracket includes a free end having a receiving portion 874 that is matable with the plunger 878. As used herein, matable means that the receiving portion 874 and the plunger 878 each comprise a shape suitable to allow the receiving portion 874 to mate with the plunger 878. For example, the receiving portion 874 may be shaped to interact with the projection 876 of the plunger 878. The selective engagement mechanism 860 may include a bracket biasing member 880 for biasing the bracket 862 into an engaged position. The plunger 878 may include a plunger biasing member to bias the plunger 878 away from the bracket 862. In another aspect of the invention, the bracket biasing member 880 is sufficient alone to bias the plunger projection 876 away from the bracket.

Operation of the selective engagement mechanism 860 will now be described. As shown in FIG. 7, in the default position, the bracket biasing member 880 biases the bracket 862 upwardly (i.e., in a direction toward the probe) such that the gear 838 is meshed with the gear 840. Also, as shown in FIG. 7, the plunger 878 is fully retracted such that the plunger projection 876 is flush with the side wall of the holster 805. In this position, because the gear 838 is meshed with the gear 840, movement of the thumbwheel 60 will transmit motion to the holder drive gear 851, which in turn transmits motion to the tissue sample holder, in the manner described above. Thus, in the default position, the rotation of the thumbwheel is directly linked with the rotation of the sample holder. When the operator wishes to interrupt the linkage such that rotation of the thumbwheel is no longer linked with rotation sample holder, the operator pushes on the plunger 878. As the operator pushes on the plunger 878, the plunger projection 876 moves away from the side wall of the holster and moves toward the receiving portion 874 of the bracket 862. This force may include overcoming a plunger biasing mechanism that biases the plunger 878 toward the retracted position. Once the plunger projection 876 contacts the receiving portion 874 the continued force against the bracket 862 imparts a downward force (i.e., away from the probe). For example, as shown in FIG. 7, the plunger projection 876 and the bracket receiving portion 874 may be inclined such that the forward motion of the plunger 878 contacting the bracket receiving portion 874 imparts the downward force. Because one end of the bracket 862 is pivotally connected to the shaft 834, the downward force causes the bracket 862 to pivot about the shaft 834. The retaining features 870, being disposed in the troughs 864 of the bracket 862, along with the gear 838 being connected to the retaining features 870, also move with the pivoting of the bracket 862. Once the bracket 838 has been pivoted the gear 838 is no longer meshed with the gear 840. With the gears being in the non-meshed position, the thumbwheel 60 is no longer linked with the holder drive gear 851 or the sample holder manifold 144. Thus, movement of the thumbwheel 60 will not impart a rotational motion on the sample holder manifold 144. Similarly, motor rotation (discussed in detail below) of the tissue sample holder manifold 144 will not impart rotational motion on the thumbwheel 60. Accordingly, the thumbwheel 60 can be freely rotated without changing the compartment to which the sample will be received and the tissue sample holder manifold 144 can be freely rotated without changing orientation of the thumbwheel 60 or needle 10. This position, where the plunger 878 is fully actuated, and the gear 838 is no longer meshed with gear 840 is shown in FIG. 8.

The plunger 878 may include a retaining mechanism 882 so that the plunger 878 will remain in the depressed position even after the operator has stopped applying force to the plunger 878. For example, the retaining mechanism 882 may include a pin 884 and an L-shaped slot 886. After fully depressing the plunger 878 the pin 884 will be located at the rear of the axial portion 888 of the L-shaped slot 886 (e.g., where the axial portion 888 meets the circumferential portion 890). Then, the operator may rotate the plunger 878 such that the pin 884 is located in the circumferential portion 890 of the L-shaped slot 886. Once located in this position, the pin 884 prevents any forward or backward movement of the plunger 878 until the operator rotates the plunger 878 back to the original position.

Figure 9:
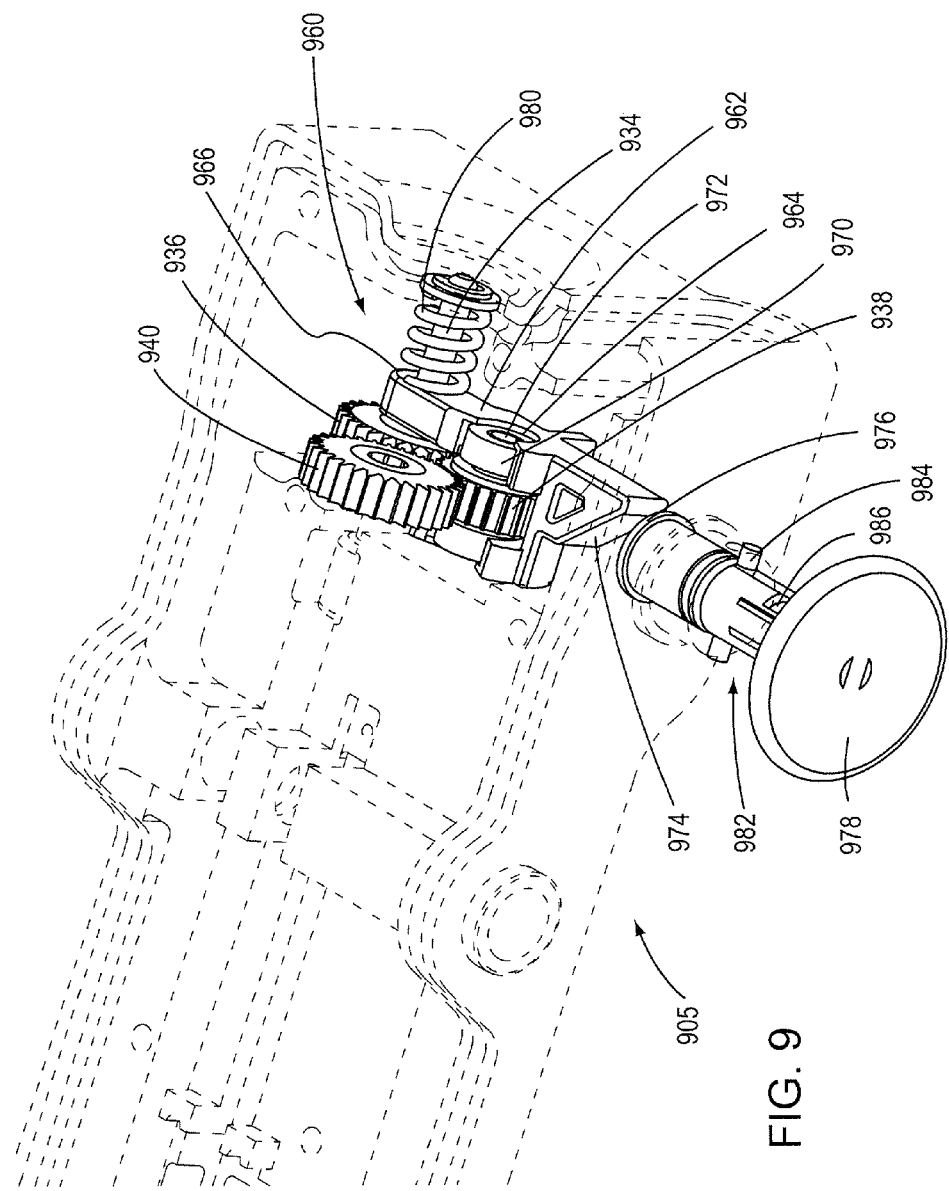
FIG. 9 is a partial perspective view of a stereotactic holster in accordance with another aspect of the present invention, with components removed.

FIG. 9 shows another example selective engagement mechanism 960, in accordance with aspects of the present invention. The selective engagement mechanism 960 may include a bracket 962 slideably connected to an end of the shaft 934. The bracket 962 may be attached to the shaft 934 by passing the shaft 934 through receiving holes 966. The bracket 962 includes a pair of troughs 964 adjacent to the gear 938 for receiving a pair of retaining features 970. The retaining features 970 and gear 938 may be attached to the shaft 972. The gear 938 may be located between the pair of retaining features 970. The retaining features 970 rest within the troughs 964 but may freely rotate along with the shaft 972 and the gear 938. Because gear 938 meshes with gear 936, rotation of the gear 936 causes the gear 938 to rotate. The selective engagement mechanism 960 further includes a plunger 978 having a projection 976. The bracket includes a free end having a receiving portion 974, shaped to interact with the projection 976 of the plunger 978. The selective engagement mechanism 960 may include a bracket biasing member 980 for biasing the bracket 962 into an engaged position. As shown in FIG. 9, the biasing member 980 may surround the shaft 934 and abut a portion of the bracket 962.

Operation of the selective engagement mechanism 960 will now be described. The bracket biasing member 980 biases the bracket 962 forwardly (i.e., in a direction toward the needle) such that the gear 938 is meshed with the gear 940. Also, as shown in FIG. 9, the plunger 978 is fully retracted such that the plunger projection 976 is flush with the side wall of the holster 905. In this position, because the gear 938 is meshed with the gear 940, movement of the thumbwheel 60 will transmit motion to the tissue sample holder drive gear (not shown), which in turn transmits motion to the tissue sample holder, in the manner described above. Thus, in the default position, the rotation of the thumbwheel is directly linked with the rotation of the sample holder. When the operator wishes to interrupt the linkage such that rotation of the thumbwheel is no longer linked with for rotation of the tissue sample holder, the operator pushes on the plunger 978. As the operator pushes on the plunger 978, the plunger projection 976 moves away from the side wall of the holster and moves toward the receiving portion 974 of the bracket 962. This force may include overcoming a plunger biasing mechanism that biases the plunger 978 toward the retracted position. Once the plunger projection 976 contacts the receiving portion 974 the continued force against the bracket 962 imparts a rearward force (i.e., away from the needle) to the bracket. For example, the plunger projection 976 and the bracket receiving portion 974 may be inclined such that the forward motion of the plunger 978 contacting the bracket receiving portion 974 imparts the rearward force. Because one end of the bracket 962 is slideably associated with the shaft 934, the rearward force causes the bracket 962 to slide along the shaft 934 in direction away from the needle. The retaining features 970, being disposed in the troughs 964 of the bracket 962, along with the gear 938 being connected to the retaining features 970, also move with the sliding of the bracket 962. Once the gear 938 has been translated toward the rear of the holster, the gear 938 is no longer meshed with the gears 940, 936. With the gears being in the non-meshed position, the thumbwheel 60 is no longer linked with the holder drive gear or the tissue sample holder manifold 144. Thus, movement of the thumbwheel 60 will not impart a rotational motion on the tissue sample holder manifold 144. Similarly, motor rotation (discussed in detail below) of the tissue sample holder manifold 144 will not impart rotational motion on the thumbwheel 60. Accordingly, the thumbwheel 60 can be freely rotated without changing the compartment to which the sample will be received and the tissue sample holder manifold 144 can be freely rotated without changing orientation of the thumbwheel 60 or needle 10.

The plunger 978 may include a retaining mechanism 982 so that the plunger 978 will remain in the depressed position even after the operator has stopped applying force to the plunger 978. For example, the retaining mechanism 982 may include a pin 984 and an L-shaped slot 986. After fully depressing the plunger 978 the pin 984 will be located at the rear of the axial portion of the L-shaped slot 986 (e.g., where the axial portion meets the circumferential portion). Then, the operator may rotate the plunger 978 such that the pin 984 is located in the circumferential portion of the L-shaped slot. Once located in this position, the pin 984 prevents any forward or backward movement of the plunger 978 until the operator rotates the plunger 978 back to the original position.

The selective engagement mechanism 860, 960 provides the operator with the ability to select when the thumbwheel 60 should be linked to the tissue sample holder 140. This allows the operator the flexibility to have 1:1 linked rotation of the thumbwheel 60 with the tissue sample holder manifold 144 and when desired, remove the linked rotation. For example, the operator can take multiple samples in the same tissue compartment (by disengaging the linkage while continuing to take samples), or can return to a previous needle orientation, without rotating the tissue sample holder (by disengaging the linkage and then rotating the needle to a previous orientation). In another aspect, the operator can unlink the thumbwheel 60 from the tissue sample holder manifold 144 by depressing the plunger 878, then rotating the tissue sample holder manifold 144 without rotating the needle 10 to inspect the quality of the sample within the tissue sample holder manifold 144. The operator can then rotate the tissue sample holder manifold 144 back to the original (or any other position) while the plunger 878, 978 remains depressed, and then allow the plunger 878 return to the unretracted position to reestablish the linkage.

Figure 10:
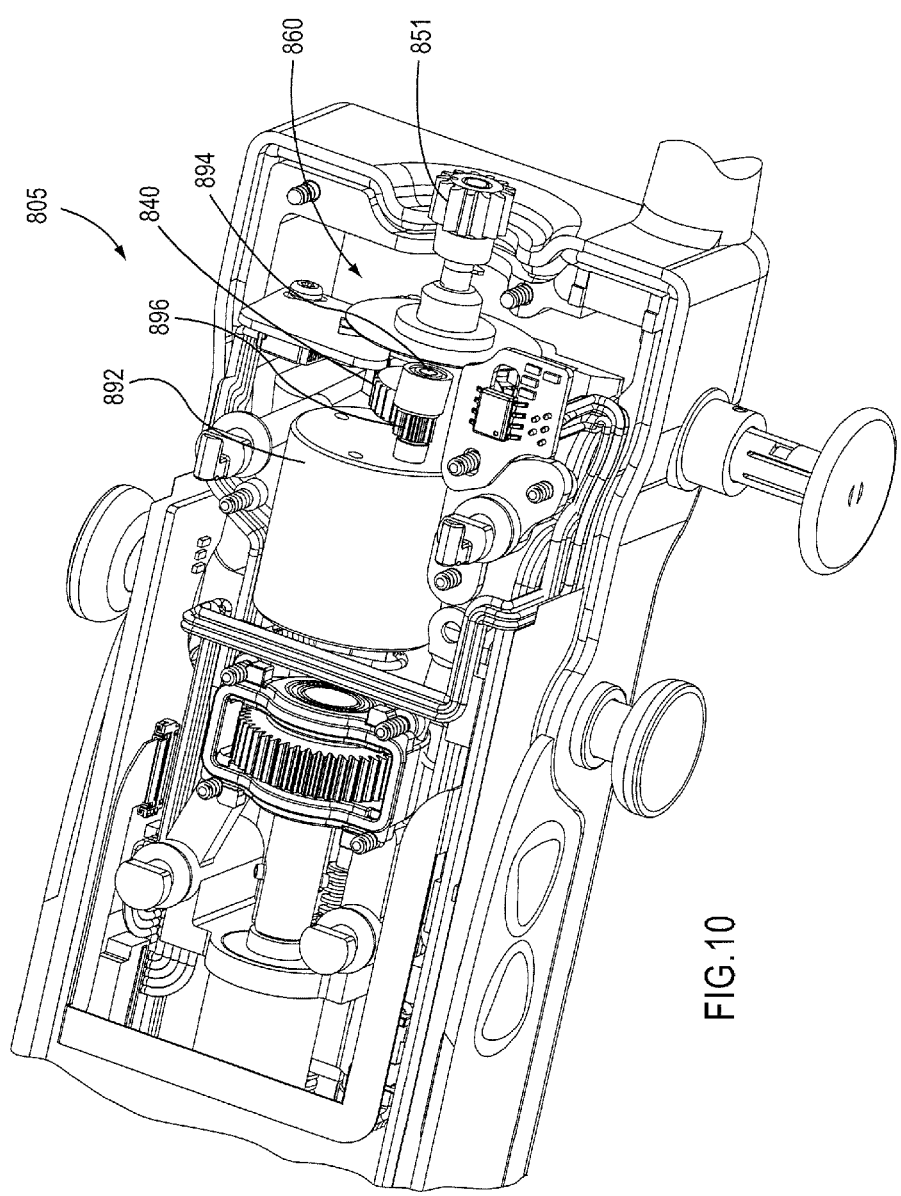
FIG. 10 is a partial perspective view of the stereotactic holster of FIG. 5, with a top housing member omitted.

As shown in FIG. 10, the tissue sample holder rotation may be controlled by a motor 892, such as a piezoelectric motor, mounted in the holster 805. The motor 892 may have shaft 894 connected to a gear 896. The gear 896 meshes with the gear 840. When the motor 892 is actuated, the shaft 894 rotates along with the gear 896. Because the gear 896 meshes with the gear 840, activation of the motor 892 imparts rotation on the gear 840, causing rotation of the gear 851. Thus, when the probe is coupled with holster 805 to engage holder drive gear 851 with the holder gear 170 and motor 892 is actuated, manifold 144 is rotated within tissue sample holder 140. When the selective engagement mechanism 860 is configured such that gear 838 is meshed with the gear 840, activation of the motor 892 will likewise cause rotation of the thumbwheel 60 and needle 10 through the linking mechanism 815. Thus, through computer control of the motor 892, the rotation of the manifold 144 and the needle 10 may be fully automatically and cooperatively. When the selective engagement mechanism 860 is configured such that the gear 838 is not meshed with the gear 840, activation of the motor 892 will only impart rotation on the manifold 144, while the needle 10 will remain stationary, unless rotated separately via the thumbwheel 60. It should be understood that the motor may also be implemented in holster 905 in a similar manner as shown in FIG. 10.

Similarly, in an aspect of the present invention, actuation of the selective engagement mechanism 860, 960 (i.e., the depression and/or rotation of the plunger 878, 978) may be performed via the computer controller. While not shown, conventional methods of electromechanically depressing the plunger 878, 978 may be implemented. The software may allow the operator to actuate the selective engagement mechanism 860, 960 by issuing a computer command. Additionally, the software may be programmed to automatically actuate the selective engagement mechanism 860, 960 according predefined parameters. Accordingly, by implementing computer software to control actuation of the motor 892, in combination with selectively engaging and disengaging the linkage between the thumbwheel 60 and the holder gear 851, a wide variety of sampling options are available.

For example, in a first setting, the computer controller will maintain selective engagement mechanism 860, 960 in a configuration where gear 838, 938 and the gear 840, 940 are meshed. In this setting, when the computer controller causes the motor to actuate, the rotation of the manifold 144 will match the rotation of the needle 1:1. This first setting would allow fully automatic sampling where each o'clock position of the needle 10 will automatically correspond with an o'clock position of the manifold. For example, at the one o'clock position of the needle 10 a sample will be taken and be stored in the one o'clock position of the manifold.

As used herein, the "o'clock position" of the needle means the orientation of the needle where the aperture of the needle is positioned to take a sample corresponding to the hour located on the face of an analog clock. For example at the "twelve o'clock position" the aperture of the needle may be facing upwardly toward the patient's head. Then, when the needle is rotated clockwise by approximately 30 degrees from the "twelve o'clock position," the second position would be the "one o'clock" position. Each consecutive rotation of the needle may correspond to an o'clock position with 12 positions being defined within one full rotation of the needle. While the needle positions are generally referred to herein as o'clock position, it should be understood that any number of positions may be defined by providing a smaller angle or greater angle between positions. For example, if each consecutive position is defined by a 15 degree rotation, then there would be 24 consecutive positions around one full rotation of the needle. Similarly, if each consecutive position is defined by a 60 degrees rotation, there would be 6 consecutive positions within one full rotation of the needle. Furthermore, the degree of rotation between positions does not have to be uniform. For example, the amount of rotation between a first position and second position may be 15 degrees, while the amount of rotation between the second position and a third position may be 30 degrees. The manifold similarly may have a plurality of chambers having "o'clock" designation that correspond with the o'clock positions of the needle. For example, the chamber of the manifold designated as the 12 o'clock position would correspond to the 12 o'clock needle position. In this example, the needle aperture would be facing upward toward the head of the patient (i.e., the 12 o'clock position), and the chamber of the manifold positioned to receive the tissue taken from this particular needle position would be the 12 o'clock chamber. The manifold may have a generally cylinder shape that is divided into a plurality of equally sized chambers. As the chambers correspond to the needle positions, the chambers may also be designated by the same number of consecutive whole numbers. As with the needle positions, the number of chambers in the manifold may be varied, but generally match the number of needle positions. For example, if there are 24 defined positions of the needle, then the manifold may have 24 chambers.

As used herein, the "position of the manifold" means that the particular tissue sample chamber associated with a given o'clock position is aligned with the sample tissue passageway to receive a vacuumed tissue sample. For example, the "one o'clock position of the manifold" means that the tissue sample chamber associated with the one o'clock position is aligned with the sample tissue passageway and will receive the tissue sample once the vacuum is created. The computer controller will then activate the motor to allow simultaneous rotation of the needle 10 and manifold 144 until both are in the two o'clock position. Next, a new sample will be taken. The process may continue automatically for as many o'clock (or other incremental steps) as necessary. Therefore, in this setting, samples can be taken automatically in sequential order (e.g., one o'clock, two o'clock, three o'clock, etc.)

In a second setting, where the computer controller also maintains selective engagement mechanism 860, 960 in a configuration where gear 838, 938 and the gear 840, 940 are meshed, the computer controller may take samples at particularly defined o'clock positions. For example, the operator may instruct the computer to take samples only at the odd o'clock intervals (e.g., 1, 3, 5, etc), to take samples only at the even o'clock intervals (e.g., 12, 2, 4, etc.), to take samples first at the odd o'clock intervals and then at the even o'clock intervals (e.g., first 1, 3, 5 etc. and then 12, 2, 4, etc.) or to take samples first at the even o'clock intervals and then at the odd o'clock intervals (e.g., first 12, 2, 4, etc. and then 1, 3, 5, etc.). Because of the coupling of the rotation of the thumbwheel with the rotation of the manifold, the o'clock position of the needle 10 will always correspond to the o'clock position of the manifold, as the long as the selective engagement mechanism 860, 960 remain in the linked configuration.

In a third setting, the computer controller can selectively disengage the gear 838, 938 from the gear 840, 940 as instructed by the software. This will allow for specific customization of which o'clock position of the needle 10 will correspond to which o'clock position of the manifold 144. For example, the operator may instruct the computer via software to take samples only at the odd o'clock positions (or just even, or odds then even, or even then odds) for the needle 10, but to fill the manifold 144 in sequential order. In this example, if the first sample is the one o'clock needle 10 position, it would go in the one o'clock manifold 144 position. The second needle 10 position would be the three o'clock (the next odd o'clock), while the manifold 144 would be in the two o'clock position. Similarly, the third needle 10 position would be in the five o'clock position, while the manifold 144 would be in the three o'clock position, and so on.

The above operation can be controlled by the computer in several ways. In a first method, starting from the one o'clock position of the needle 10 and the manifold 144, a sample would be taken. Then the computer would actuate the selective engagement mechanism 860, 960 to decouple the gear 838, 938 from the gear 840, 940. While still decoupled, the computer controller would actuate the motor 892 which would cause only rotation of the manifold 144. The computer controller will continue to rotate the manifold 144 until the two o'clock position is positioned two positions away from the position aligned with the tissue sample passage. Once in position, the computer controller will stop activating the motor 892 and will release the selective engagement mechanism 860, 960 to mesh the gear 838, 938 with gear 840, 940, thereby restoring the linkage between the needle 10 and the manifold 144. Next, the computer controller will reactivate the motor 892, while rotating the needle 10 (thumbwheel 60) and the manifold 144 simultaneously. After rotating the needle 10 and the manifold two o'clock positions, the computer controller will cease activation of the motor. Because the needle 10 was in the one o'clock position when the rotation started, it will end at the three o'clock position. Because the manifold 144 was two o'clock positions away from the tissue sample passage, the two o'clock position of the manifold 144 will be aligned with tissue sample passage. Thus, when the vacuum begins, the needle 10 is at the three o'clock position, while the manifold 144 is in the two o'clock position. The above steps can be repeated as necessary to place the tissue sample taken at the five o'clock needle 10 position into the three o'clock manifold chamber, the tissue sample taken at the seven o'clock position in the four o'clock manifold chamber, and so on. The same technique can be used to put any tissue sample of a given o'clock needle 10 position into any desired o'clock manifold chamber.

Another method achieves the same result without any decoupling of the gear 838, 938 from the gear 840, 940. The method involves first cutting the sample at the desired o'clock position of the needle 10, but before initiating the vacuum, rotating the needle 10 and manifold 144 together until the desired manifold 144 position is acquired. For example, starting from the one o'clock position of the needle 10 and the one o'clock position of the manifold 144, it may be desirable to take a tissue sample at the three o'clock position of the needle 10 but insert that sample into the two o'clock chamber of the manifold 144. First, the computer controller would activate the motor until both the needle 10 and the manifold 144 are at the three o'clock position. After terminating the rotation, the cutter would be actuated to cut the sample. Next, before the vacuum is initiated, the computer controller will activate the motor to cause both the needle 10 and the manifold 144 to rotate to the two o'clock position. Then, the vacuum is initiated, to bring the already cut tissue sample into the two o'clock chamber of the manifold 144. The above steps can be repeated as necessary to place the tissue sample taken at the five o'clock needle 10 position into the three o'clock manifold chamber, the tissue sample taken at the seven o'clock position in the four o'clock manifold chamber, and so on. The same technique can be used to put any tissue sample of a given o'clock needle 10 position into any desired o'clock manifold chamber.

In another aspect of the present invention a separate motor may independently control the needle 10. The needle motor would likewise be controlled by the computer controller and would operate directly on the needle 10. When a needle motor is present, the o'clock position of the needle 10 can be selected independently of the o'clock position of the manifold 144. For example, when it is desirable to put the tissue sample taken at the three o'clock position in the two o'clock chamber of the manifold 144, the computer controller would first decouple the gear 838, 938 from the gear 840, 940 by actuating the selective engagement mechanism 860, 960. Then, the computer controller would independently control the manifold motor 892 and the needle rotation motor until the needle 10 is in the three o'clock position and the manifold 144 is in the two o'clock position. The above steps can be repeated as necessary to place the tissue sample taken at the five o'clock needle 10 position into the three o'clock manifold chamber, the tissue sample taken at the seven o'clock position in the four o'clock manifold chamber, and so on. The same technique can be used to put any tissue sample of a given o'clock needle 10 position into any desired o'clock manifold chamber.

In another aspect of the present invention a combination of automatic and manual actuation may be used to obtain the desired tissue sample in the desired manifold chamber. For example, when it is desirable to put the tissue sample taken at the three o'clock position in the two o'clock chamber of the manifold 144, the computer controller will first decouple the gear 838, 938 from the gear 840, 940 by actuating the selective engagement mechanism 860, 960. Alternatively, the operator can manually disengage the gears by pressing and/or rotating the plunger 878, 978. Once decoupled, the user can manually rotate the thumbwheel 60 until the needle 10 is in the three o'clock position, while the computer controller will activate the motor to rotate the manifold 144 until it is in the two o'clock position. Then, the sample can be taken. The above steps can be repeated as necessary to place the tissue sample taken at the five o'clock needle 10 position into the three o'clock manifold chamber, the tissue sample taken at the seven o'clock position in the four o'clock manifold chamber, and so on. The same technique can be used to put any tissue sample of a given o'clock needle 10 position into any desired o'clock manifold chamber.

In another aspect of the present invention, the operator may wish to rotate the manifold 144 so that collected tissue sample may be collected. To do this, the operator may manually (or automatically via the computer controller) unlink the thumbwheel 60 from the manifold 144 by depressing the plunger. Once unlinked, the computer controller can activate the motor 892 to rotate the manifold 144 until the particular o'clock position is viewable by the operator. After the inspection is completed, the computer controller will activate the motor to either return the sample chamber just viewed back to the previous position (or any other position). Once returned, the operator can allow the link between the thumbwheel and the manifold 144 to return by manually (or automatically via the computer controller) allowing the plunger to retract.

An encoder 253, illustrated in FIG. 2, and described in detail in the '687 patent, may be used in conjunction with the motor 892 and computer controller to sense rotational movement of the piezoelectric motor and to indirectly measure movement of the manifold 144 within the tissue sample holder.

In another aspect, the user may implement the above-described functionality via a computer having a graphical user interface (GUI). For example, the user may select a configuration on the graphical user interface that allows the system to perform the above-described steps to deposit tissue into programmable chambers such that certain o'clock positions are skipped. For example, the GUI may be configured such that after receiving the user's input, the samples are taken at only odd o'clock positions and deposited in their corresponding manifold chamber by following the above-described steps or similar steps that provide the same result. A computer system and communication system, including computer logic, for providing the GUI and for implementing the user's instructions are discussed below. An example GUI is disclosed in U.S. Provisional Application No. 61/682,418, entitled "BIOPSY SYSTEM WITH GRAPHICAL USER INTERFACE," filed on Aug. 13, 2012, which is incorporated by reference herein.

In another aspect, the user would enable the configuration as per above, but the system would deposit the samples in sequential chambers, such that odd numbered clock positions would be deposited in sequentially numbered chambers."

Figure 11:
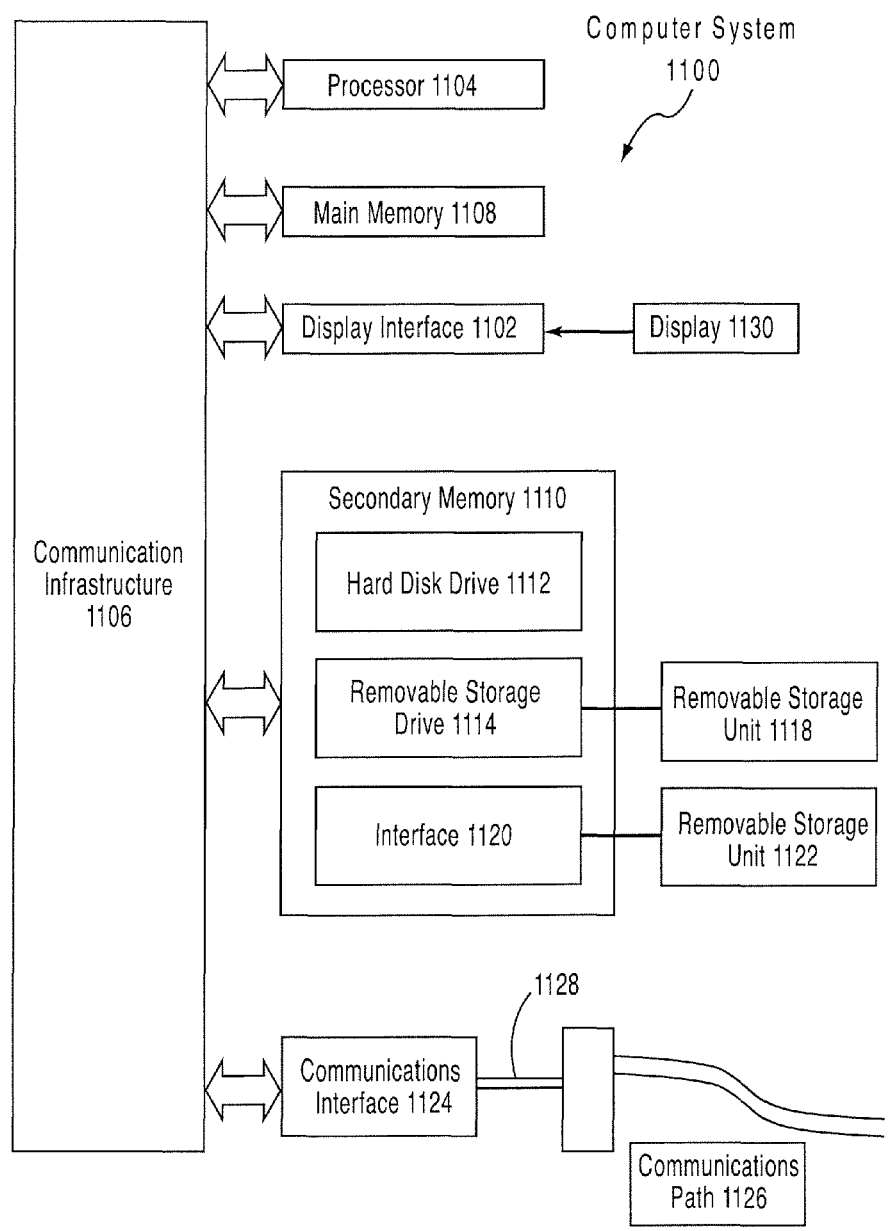
FIG. 11 presents an example system diagram of various hardware components and other features, for use in accordance with aspects of the present invention.

In some variations, aspects of the present invention may be directed toward one or more computer systems capable of carrying out the functionality described herein. An example of such a computer system 1100 is shown in FIG. 11.

Computer system 1100 includes one or more processors, such as processor 1104. The processor 1104 is connected to a communication infrastructure 1106 (e.g., a communications bus, cross-over bar, or network). Various software aspects are described in terms of this example computer system. After reading this description, it will become apparent to a person skilled in the relevant art(s) how to implement the invention using other computer systems and/or architectures.

Computer system 1100 can include a display interface 1102 that forwards graphics, text, and other data from the communication infrastructure 1106 (or from a frame buffer not shown) for display on a display unit 1130. Computer system 1100 also includes a main memory 1108, preferably random access memory (RAM), and may also include a secondary memory 1110. The secondary memory 1110 may include, for example, a hard disk drive 1112 and/or a removable storage drive 1114, representing a floppy disk drive, a magnetic tape drive, an optical disk drive, etc. The removable storage drive 1114 reads from and/or writes to a removable storage unit 1118 in a well-known manner. Removable storage unit 1118, represents a floppy disk, magnetic tape, optical disk, etc., which is read by and written to removable storage drive 1114. As will be appreciated, the removable storage unit 1118 includes a computer usable storage medium having stored therein computer software and/or data.

In alternative aspects, secondary memory 1110 may include other similar devices for allowing computer programs or other instructions to be loaded into computer system 1100. Such devices may include, for example, a removable storage unit 1122 and an interface 1120. Examples of such may include a program cartridge and cartridge interface (such as that found in video game devices), a removable memory chip (such as an erasable programmable read only memory (EPROM), or programmable read only memory (PROM)) and associated socket, and other removable storage units 1122 and interfaces 1120, which allow software and data to be transferred from the removable storage unit 1122 to computer system 1100.

Computer system 1100 may also include a communications interface 1124. Communications interface 1124 allows software and data to be transferred between computer system 1100 and external devices. Examples of communications interface 1124 may include a modem, a network interface (such as an Ethernet card), a communications port, a Personal Computer Memory Card International Association (PCMCIA) slot and card, etc. Software and data transferred via communications interface 1124 are in the form of signals 1128, which may be electronic, electromagnetic, optical or other signals capable of being received by communications interface 1124. These signals 1128 are provided to communications interface 1124 via a communications path (e.g., channel) 1126. This path 1126 carries signals 1128 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 1114, a hard disk installed in hard disk drive 1112, and signals 1128. These computer program products provide software to the computer system 1100. The invention is directed to such computer program products.

Computer programs (also referred to as computer control logic) are stored in main memory 1108 and/or secondary memory 1110. Computer programs may also be received via communications interface 1124. Such computer programs, when executed, enable the computer system 1100 to perform the features of the present invention, as discussed herein. In particular, the computer programs, when executed, enable the processor 1110 to perform the features of the present invention. Accordingly, such computer programs represent controllers of the computer system 1100.

In an aspect where the invention is implemented using software, the software may be stored in a computer program product and loaded into computer system 1100 using removable storage drive 1114, hard drive 1112, or communications interface 1120. The control logic (software), when executed by the processor 1104, causes the processor 1104 to perform the functions of the invention as described herein. In another aspect, the invention is implemented primarily in hardware using, for example, hardware components, such as application specific integrated circuits (ASICs). Implementation of the hardware state machine so as to perform the functions described herein will be apparent to persons skilled in the relevant art(s).

In yet another aspect, the invention is implemented using a combination of both hardware and software.

Figure 12:
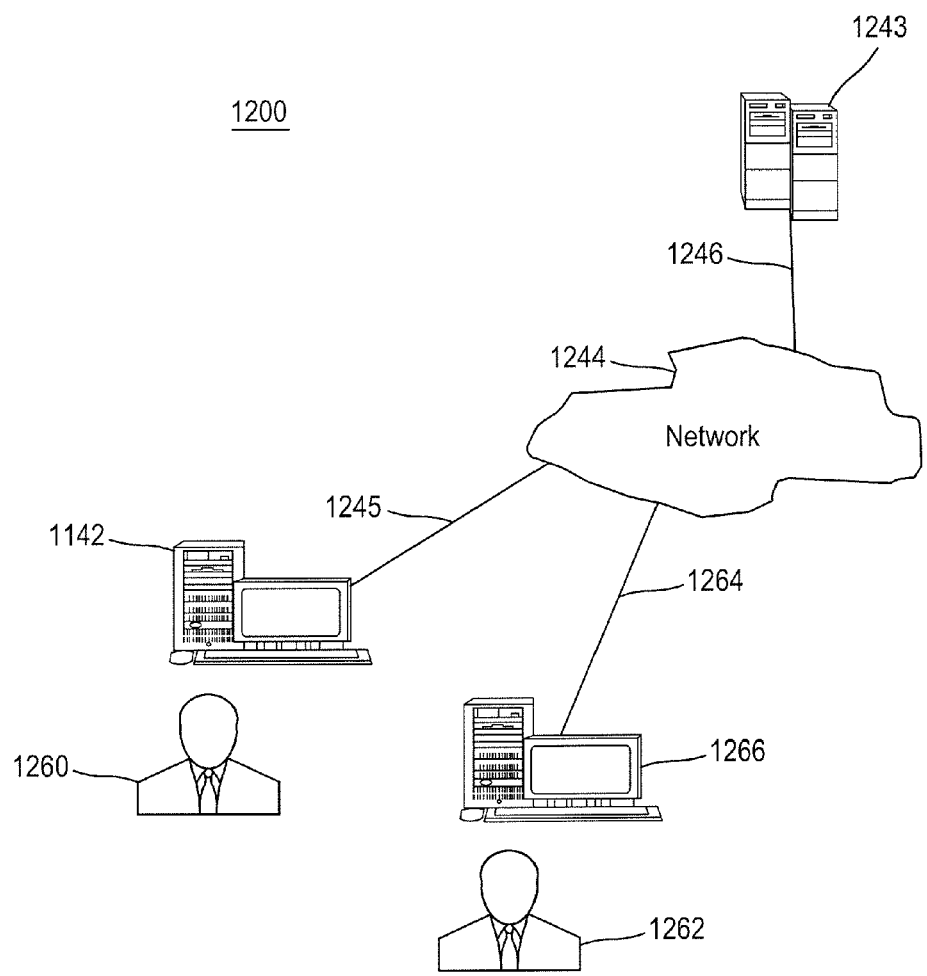
FIG. 12 is a block diagram of various example system components, for use in accordance with aspects of the present invention.

FIG. 12 shows a communication system 1200 involving use of various features in accordance with aspects of the present invention. The communication system 1200 includes one or more assessors 1260, 1262 (also referred to interchangeably herein as one or more "users") and one or more terminals 1242, 1266 accessible by the one or more accessor 1260, 1262. In one aspect, operations in accordance with aspects of the present invention is, for example, input and/or accessed by an accessor 1260 via terminal 1242, such as personal computers (PCs), minicomputers, mainframe computers, microcomputers, telephonic devices, or wireless devices, such as personal digital assistants ("PDAs") or a hand-held wireless devices coupled to a remote device 1243, such as a server, PC, minicomputer, mainframe computer, microcomputer, or other device having a processor and a repository for data and/or connection to a repository for data, via, for example, a network 1244, such as the Internet or an intranet, and couplings 1245, 1264. The couplings 1245, 1264 include, for example, wired, wireless, or fiberoptic links. In another aspect, the method and system of the present invention operate in a stand-alone environment, such as on a single terminal. The communication system may include the graphical user interface disclosed in U.S. Provisional Application No. 61/682,418, entitled "BIOPSY SYSTEM WITH GRAPHICAL USER INTERFACE," filed on Aug. 13, 2012, which is incorporated by reference herein.

While this invention has been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects of the invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents.

The invention claimed is:

1. A biopsy system comprising:
   (a) a probe assembly, wherein the probe assembly comprises a probe body, a needle, and a thumbwheel, wherein the needle is rotatable about a longitudinal axis;
   (b) a holster, wherein the holster is selectably attachable to the probe body, wherein the holster is configured to communicate with the thumbwheel when coupled to the probe body;
   (c) a tissue sample holder, wherein the tissue sample holder comprises a rotatable member comprising a plurality of chambers; and
   (d) a linking mechanism, wherein the linking mechanism is configured to communicate rotation of the thumbwheel to rotation of the rotatable member of the tissue sample holder, wherein the linking mechanism comprises a selective engagement mechanism, wherein the selective engagement mechanism is configured to selectably transition the linking mechanism between a first configuration and a second configuration, wherein the linking mechanism is configured to associate rotation of the thumbwheel with rotation of the rotatable member of the tissue sample holder when in the first configuration, wherein the linking mechanism is configured to disassociate rotation of the thumbwheel with rotation of the rotatable member of the tissue sample holder when in the second configuration.

2. The biopsy system of claim 1, wherein the thumbwheel comprises a plurality of teeth.

3. The biopsy system of claim 1, wherein the holster comprises a recess, wherein the recess is configured to align with the thumbwheel.

4. The biopsy system of claim 3, wherein the holster further comprises a first gear extending at least partially into the recess, wherein the first gear is configured to communicate rotation between the linking mechanism and the thumbwheel.

5. The biopsy system of claim 4, wherein the selective engagement mechanism includes a movable gear in communication with a shaft extending proximally from the first gear.

6. The biopsy system of claim 5, wherein the movable gear of the selective engagement mechanism is movable to transition the linking mechanism between the first configuration and the second configuration.

7. The biopsy system of claim 6, wherein the selective engagement mechanism further includes a button assembly, wherein a portion of the button assembly is in communication with the movable gear.

8. The biopsy system of claim 7, wherein the button assembly includes a push button and a rod.

9. The biopsy system of claim 8, wherein the rod of the button assembly is in communication with the movable gear, wherein the push button is configured to drive the rod to move the movable gear and thereby transition the linking mechanism between the first configuration and the second configuration.

10. The biopsy system of claim 1, wherein the thumbwheel is positioned for operation of the biopsy system with a single hand.

11. The biopsy system of claim 1, wherein the selective engagement mechanism comprises a bracket, a first gear, a first rotatable shaft, and a second gear.

12. The biopsy system of claim 11, wherein the first gear of the selective engagement mechanism is coupled with the bracket, wherein the bracket is movable such that movement of the bracket moves the first gear.

13. The biopsy system of claim 12, wherein the first rotatable shaft of the selective engagement mechanism extends toward the thumbwheel, wherein the second gear is coupled to the first rotatable shaft of the selective engagement mechanism such that the second gear rotates upon rotation of the first rotatable shaft.

14. The biopsy system of claim 13, wherein the bracket is coupled to and is movable about the rotatable shaft.

15. The biopsy system of claim 13, wherein the bracket is movable to transition the linking mechanism between the first configuration and the second configuration.

16. A biopsy system comprising:
(a) a body;
(b) a needle extending distally from the body;
(c) a thumbwheel associated with the needle, wherein the thumbwheel is configured to rotate the needle about a longitudinal axis;
(d) a tissue sample holder comprising a rotatable member; and
(e) a selective engagement mechanism, wherein the selective engagement mechanism is configured to selectively engage and disengage communication of rotation between the thumbwheel and the rotatable member of the tissue sample holder.

17. The biopsy system of claim 16, wherein the selective engagement mechanism includes a first shaft, a second shaft, a third shaft, and a movable gear.

18. The biopsy system of claim 17, wherein the first shaft extends from the movable gear to the thumbwheel, wherein the second shaft extends from the thumbwheel to the needle, wherein the third shaft extends from the movable gear to the tissue sample holder.

19. The biopsy system of claim 17, wherein the movable gear is in selective communication with the first shaft and the third shaft, wherein the movable gear is selectively movable to engage and disengage communication of rotation between the thumbwheel and the rotatable member of the tissue sample holder.

20. A biopsy system comprising:
(a) a body;
(b) a needle extending distally from the body;
(c) a thumbwheel associated with the needle, wherein the thumbwheel is configured to rotate the needle about a longitudinal axis;
(d) a tissue sample holder comprising a rotatable member; and
(e) a motor, wherein the motor is configured to selectively couple to the tissue sample holder and the needle, wherein the motor is configured to selectively decouple from the tissue sample holder to thereby only rotate the needle.

* * * * *